United States Patent

Berthiaume et al.

[11] Patent Number: 5,830,446
[45] Date of Patent: Nov. 3, 1998

[54] FLUORESCENT BRIGHTENING OF COSMETIC COMPOSITIONS

[75] Inventors: Marianne D. Berthiaume, Latham; William J. Raleigh, deceased, late of Rensselaer, by Marylyn T. Raleigh, legal representative; Richard J. Uriarte, Clifton Park, all of N.Y.

[73] Assignee: General Electric Company, Waterford, N.Y.

[21] Appl. No.: 859,464

[22] Filed: May 19, 1997

Related U.S. Application Data

[63] Continuation of Ser. No. 561,652, Nov. 17, 1995, abandoned.

[51] Int. Cl.$^6$ ............... A61K 7/11; A61K 7/043; A61K 7/027
[52] U.S. Cl. ............... 424/70.1; 424/47; 424/61; 424/63; 424/64; 424/401
[58] Field of Search ............... 424/701, 401, 424/47, 61, 63, 64

[56] References Cited

U.S. PATENT DOCUMENTS

| | | | |
|---|---|---|---|
| 3,875,071 | 4/1975 | Grand | 252/106 |
| 4,067,903 | 1/1978 | Hoch et al. | 260/570.6 |
| 4,108,800 | 8/1978 | Froehlich | 252/541 |
| 4,312,855 | 1/1982 | Grand | 424/59 |
| 4,441,885 | 4/1984 | Abel et al. | 8/603 |
| 4,453,946 | 6/1984 | Abel et al. | 8/603 |
| 4,615,593 | 10/1986 | Neefe | 351/162 |
| 4,657,363 | 4/1987 | Neefe | 351/162 |
| 4,705,525 | 11/1987 | Abel et al. | 8/555 |
| 4,705,526 | 11/1987 | Abel et al. | 8/555 |
| 5,445,655 | 8/1995 | Kuhn et al. | 8/555 |

FOREIGN PATENT DOCUMENTS

| | | |
|---|---|---|
| 0 370 470 A2 | 11/1989 | European Pat. Off. |
| 820111 | 3/1956 | United Kingdom . |
| 825413 | 8/1957 | United Kingdom . |
| 1 328 108 | 1/1970 | United Kingdom . |

*Primary Examiner*—Jyothsna Venkat
*Attorney, Agent, or Firm*—Kenneth S. Wheelock

[57] ABSTRACT

Fluorescent brightening compounds increase the apparent color intensity or shine of cosmetic compositions.

9 Claims, No Drawings

FLUORESCENT BRIGHTENING OF COSMETIC COMPOSITIONS

This is a continuation of application(s). Ser. No. 08/561,652 filed on Nov. 17, 1995 now abandoned.

FIELD OF THE INVENTION

The present invention relates to cosmetic compositions containing a fluorescent compound that brightens and intensifies the shine or color of the cosmetic or personal care composition applied to the underlying skin or hair.

BACKGROUND OF THE INVENTION

Cosmetics are used to enhance personal appearance. The enhancement of color, shine and luster are properties of cosmetic formulations that are very desirable from the standpoint of product function as defined by the consumer using the cosmetics. Shine or luster is defined as the ratio of specular reflection to diffuse reflection of light. Consumers evaluate luster by comparing the shiny or reflective portion of a surface to the dull or less reflective portion of a surface. By such a subjective test, two surfaces possessing equivalent specular and diffuse reflective powers will appear different to the human observer depending on the color. Under these conditions, the darker surface would appear more lustrous to the untrained human observer, i.e. most consumers.

This analysis leads to the conclusion that one method of improving the apparent luster or shine of human hair for example is to color the hair with a darker shade. Darkening the color shade of hair to improve apparent luster is not an acceptable mode of shine or luster enhancement to a significant number of cosmetic consumers who possess or desire hair having a light color.

A second method of increasing the apparent luster of hair is to coat the hair with a material having a high refractive index, preferably a refractive index close to or slightly higher than that of the surface. Human hair has a refractive index of 1.51 to 1.52. Many hair care cosmetic formulations for enhancing apparent luster or shine incorporate phenyltrimethicone fluids ($M_3T'$ where the T' group is phenyl substituted) which have a refractive index of 1.46. Other materials used for this purpose include balsam copaiba (refractive index=1.49) and mineral oil (refractive index=1.476).

SUMMARY OF THE INVENTION

The present invention provides for imparting increases in the apparent luster or shine of hair or increases in the apparent color intensity of color cosmetics through incorporating fluorescent brighteners in the cosmetic compositions. Thus the present invention provides for a method for increasing the apparent shine on hair comprising:

1) formulating a cosmetic composition suitable for application to human hair and
2) adding thereto a fluorescent brightening agent.

The present invention also provides for a method for increasing the apparent color intensity of a cosmetic composition comprising:

1) formulating a cosmetic composition suitable for application to the human body and
2) adding thereto a fluorescent brightening agent.

Preferred fluorescent brightening agents are selected from the group consisting of:

1) 2, 2'-(2, 5-thiophene diyl)bis(5-tert-butylbenzoxazole);
2) 2, 2'-(1, 1-ethylene bis(3-sulfo-4, 1-phenylene)imino (6-(diethyl amino)-1, 3, 5-triazine-4, 2-di-yl)imino)) bis-1, 4-benzene-di-sulfonic acid, hexa-sodium salt;
3) 4-methyl-7, 7-dimethyl-amino-coumarin; and
4) 4-methyl-7, 7-diethyl-amino-coumarin.

Cosmetic compositions that may be rendered improved by the process of the present invention are hair care products such as conditioners, mousses, gels, cuticle coats and the like and color cosmetics such as lipsticks and nail enamels or lacquers.

DETAILED DESCRIPTION OF THE INVENTION

The control of specular versus diffuse reflectance in cosmetic formulations is a function of the appearance enhancing characteristics desired for the cosmetic composition. For example, gloss, i.e. a high specular reflectivity is usually undesirable in face powders and the like where a matte or flat finish is desirable. In contrast, for hair care formulations, lipsticks, nail enamels and the like it is frequently desirable to increase gloss, i.e. the ratio of specular to diffuse reflectance.

The present invention is based on the discovery that the addition of small quantities of fluorescent compounds added to cosmetic formulations increases the apparent luster, shine or color intensity of the composition. Further, the present invention extends to translucent or opaque color cosmetic formulations such as lipsticks, nail enamels and the like where the incorporation of fluorescent brightening compounds into the composition increases the apparent color intensity.

The typical understanding of the relationship between specular and diffuse reflectance as it relates to cosmetic formulations is that increasing the refractive index of a composition increases the apparent luster of the cosmetic formulation when applied to parts of the human body. However, it has unexpectedly been found that incorporation of small amounts of fluorescent compounds into these formulations while not in quantity sufficient to affect the refractive index of the composition does impart significant apparent benefits in terms of perceived apparent luster or shine and color intensity.

Modern cosmetic formulations for hair care typically utilize various silicones in two ways to increase shine or apparent luster. First, materials such as dimethicone fluids and gums are used to provide conditioning benefits resulting in increased fiber alignment and thus a smoother surface from which to reflect light The second and more widely used method is to coat the hair with a material of high refractive index, typically a phenyl modified silicone such as phenyltrimethicone, phenylmethyl polysiloxane, or diphenyldimethicone. The concept underlying this approach is that the light is being reflected by the underlying melanin granules. Thus if the surface of the hair is coated with a material that has an index of refraction close to that of the hair cuticle, there will be less scattering of light as the light passes through the various cuticle-cuticle or cuticle-cortex interfaces.

Shine enhancing additives may be effectively added to a variety of hair care products, most commonly cuticle coats and finishing sprays. Other products such as fixatives, creams, mousses, styling gels, and the like as well could thus contain small amounts of fluorescent brightening compounds to increase the apparent luster of the hair. Applicants note that products designed to improve the luster of human hair will also improve the luster or shine of non-human hair and so these formulations may also be used for animal grooming and appearance.

Thus for example, the incorporation of 0.01 weight percent of a fluorescent compound, Uvitex OB® (available from Ciba-Geigy), 2, 2'-(2, 5-thiophene diyl)bis(5-tert-butylbenzoxazole), into a low molecular weight silicone fluid, dimethicone (polydimethylsiloxane), does not change the refractive index from that of the unmodified fluid itself, 1.4044. Yet it has been found that when the fluorescent compound, 2, 2'-(2, 5-thiophene diyl)bis(5-tert-butylbenzoxazole), is incorporated into hair care cosmetic formulations, improvements in shine on hair result by comparison to formulations containing a known luster enhancing agent, phenyltrimethicone. Thus, hair care compositions designed for a finishing application, conditioners, mousses, fixatives, pump or aerosol sprays, gels, creams, cuticle coats and the like, may contain a fluorescent additive as a shine or color enhancing additive, thereby improving the benefit of the cosmetic product This observation translates to other color cosmetic formations as well, e.g. nail lacquers, lipsticks, eye shadows, and mascaras. Nail lacquers are the largest group of manicure cosmetics. When initially introduced as a cosmetic product, the only acceptable colors for nail lacquers were either pale pink or colorless. As presently formulated, nail lacquers are available in a wide variety of colors and hue.

A nail lacquer or nail enamel is composed essentially of a film forming material, dissolved in a biocompatible volatile solvent The film forming material should be capable of dispersing or supporting colorant materials and when dry form a smooth glossy continuous coating on the nails.

The use of a lacquer type formulation in a cosmetic application requires many considerations. First, and most importantly, the formulation should be innocuous to the nails and the surrounding skin. Preferably the formulations should be non-staining so they can be conveniently removed and different colors applied if it is so desired. The formulation should be easy to apply providing an even coverage with good wetting and flow as well as having a relatively short drying time, i.e. a matter of one or two minutes at the most The film formed by the nail lacquer should be glossy, tough and flexible having a good adhesion to the nail. While the dried nail lacquer should be resistant to water and detergent solutions, it should also be permeable to oxygen, carbon dioxide and water vapor because it is being overlaid on biological material. Further, in addition to all these durability characteristics, when the user desires to remove the nail lacquer it should be easily removable.

The most typical film forming material used for nail lacquers is nitrocellulose, produced by reaction of a mixture of nitric and sulfuric acids on cotton or wood pulp. The degree of nitration and the degree of polymerization of the cellulose chain governs the viscosity of the nitrocellulose. Suitable solvents are normally ketones and esters with ethyl acetate generally being the preferred solvent Additionally other solvents are added to facilitate the addition of plasticizers and secondary resins.

Nail lacquers thus contain a basic film forming polymer such as nitrocellulose, primary solvents such as ketones and esters, co-solvents such as alcohols to enhance the solubility of other components, secondary resins such as the condensation product of para-toluene sulphonamide and formaldehyde, plasticizers, pigments, pearling agents, ultraviolet absorbers and biological materials such as proteins. The ultraviolet absorbers absorb damaging ultraviolet radiation protecting the integrity of the nail lacquer.

Another color cosmetic benefiting from fluorescent brightening of the pigment is lipstick. The compounding criteria for lipsticks are quite different from those of nail lacquers. While ideally both a nail lacquer and a lipstick must be dermatologically safe, the lipstick must be edible since it is applied to the lips. Since lipsticks are applied to the lips, the ingredients used in the formulation must have both an agreeable taste and odor. As in nail lacquers, the film forming characteristics of lipsticks are important as lipsticks should not bloom, sweat or produce excrescences. Further like nail lacquers they should be waterproof. Unlike nail lacquers they should be formulatable into a material that can form a stick that will pay-off as it is moved over the lips or a material that is easy to apply as a roll-on, color wand or lip pencil formulation as it is moved over the lips. Since no single material will function in this manner, lipsticks are a complex blend of oils, waxes, and other fatty materials.

In order to function as lipsticks, the blend of oily and waxy materials that provides the pay-off or deposition onto the lips must also function as a pigment carrier. Early lipstick pigments were based on carmine and were followed by eosin, 2, 4, 5, 7-tetrabromo fluorescein (D & C No. 21). This has been supplanted by oxide pigments, e.g. aluminum and barium lakes, and by converting otherwise soluble dyes into insoluble forms. Because lipsticks are complex mixtures of oils and waxes that melt at differing temperatures slightly above body temperature, compounding to achieve uniform properties, ease of manufacture, and stability during use by the consumer results in limiting the selection of pigments. The addition of a brightening agent such as a fluorescent brightening agent, extends the utility of the existing pigments creating a color enhanced product The brightening composition may be added into the lipstick composition containing the coloring pigment to be enhanced or it may be formulated separately into an undercoat or an overcoat composition that is separately applied but still functions to brighten color.

The addition of fluorescent compounds such as:
1) Uvitex OB® (available from Ciba-Geigy), 2, 2'-(2, 5-thiophene diyl)bis(5-tert-butylbenzoxazole);
2) Tinopal SFP® (available from Ciba-Geigy), 2, 2'-(1, 1-ethylene bis(3-sulfo-4, 1-phenylene)imino(6-(diethyl amino)-1, 3, 5-triazine4, 2-di-yl)imino))bis-1, 4-benzene-di-sulfonic acid, hexa-sodium salt; and
3) Calcofluor-LD® (available from BASF), 4-methyl-7, 7-dimethyl-amino-coumarin;
4) Calcofluor-RWP® (available from BASF), 4-methyl-7, 7-diethyl-amino-coumarin; to the pigment formulation increases the apparent color intensity for a given color pigment formulation. Other fluorescent brightening compounds such as those belonging to the triazinylstilbenes and amino-coumarins may be added for similar effects. Fluorescent compounds basically absorb light at one wavelength and re-emit it at another. Frequently, this absorption is at the blue or ultraviolet end of the spectrum and the emission is at a lower wavelength in the visible region. This absorption and re-emission of light increases the perceived color or shine of the cosmetic product.

These compounds may be employed in cosmetic formulations in a wide variety of levels, ranging from 0.0005 to 5.000 weight percent, preferably from 0.0005 to 2.500 weight percent, more preferably from 0.005 to 1.000 weight percent, and most preferably from 0.005 to 0.500 weight percent These fluorescent brightening compounds are soluble in many of the bases or solvents utilized to prepare cosmetic formulations. Depending on the particular fluorescent brightener chosen, the material may be formulated into anhydrous, aqueous, or hydro-alcoholic delivery systems. A partial list of the solvents suitable not only as carriers for cosmetics but also as carriers for the fluorescent brighteners are:
1-methyl-2-pyrrolidinone,
1N acetic acid
n-butanol,
alkyl methicones,
cyclohexane,
cyclomethicone,
diethylene glycol,
diethylene glycol monobutylether
dimethicone,
dimethiconol,
dipropylene glycol,
95 % ethanol,
ethoxy diglycol,
ethoxyethanol,
ethyl acetate,
n-heptane,
n-hexane,
0.1N hydrochloric acid,
isopropanol,
methyl ethyl ketone,
phenyltrimethicone,
tetrahydronaphthalene,
triethylene glycol,
water and mixtures thereof. Additional solvents suitable for use with the compositions of the present invention are listed in the International Cosmetic Ingredient Dictionary, Fifth Edition, Edited by John A. Wenninger and G. N. McEwen, Jr., and published by the Cosmetic Toiletry and Fragrance Association, Washington D. C. (1993).

EXPERIMENTAL

Experimental Cuticle Coat

Qualitative evaluations were performed to assess the apparent shine imparted by several cosmetic formulations on medium brown human hair. The evaluations were conducted on Caucasian hair tresses using a scale of 1 through 5 with level 1 characterized as relaxed African-American hair soaked in hexane for 5 minutes being dull and level 5 characterized as Oriental hair treated with mineral oil being shiny.

The 2, 2'-(2, 5-thiophene diyl)bis(5-tert-butylbenzoxazole) was dissolved in 350 centistoke dimethicone fluid at a concentration of 0.01 weight percent. The dimethicone solution was further diluted to a concentration of 20% in cyclomethicone, an 85:15 blend of octamethylcyclotetrasiloxane and decamethylcyclopentasiloxane, yielding a final active concentration of 0.002 weight percent active fluorescent brightener. This diluted solution was sprayed onto a 6 inch 2 g hair tress using a pump spray, depressing the valve three times per side per tress, delivering a total of 0.6 g of solution per tress, or 0.0012 g 2, 2'-(2, 5-thiophene diyl)bis(5-tert-butylbenzoxazole). All tresses were prepared from medium brown Caucasian human hair. An in-house panel of 21 participants rated the tresses treated with the fluorescent brightener as being more lustrous, or having a higher level of shine as compared to the controls.

The controls were:
1) a shampooed tress receiving no conditioning treatment,
2) a shampooed tress treated with a commercially available shine spray, Citrishine®, and
3) a shampooed tress treated with a silicone based cuticle coat product containing phenyltrimethicone a known luster enhancing agent All tresses were allowed to air dry prior to evaluation.

TABLE 1

Results of Luster Evaluations on Hair

| Treatment | Rating |
|---|---|
| Untreated control | 2.9 |
| Cuticle Coat | 3.5 |
| Commercial Shine Spray | 3.3 |
| Solution of Uvitex OB ® | 4.2 |

The commercial shine spray and the cuticle coat both increased the apparent luster of human hair compared to the untreated control. The composition containing the optical brightener or fluorescent brightener increased shine beyond that obtained with known luster enhancing compounds. The effect achievable with the fluorescent brightener is not related to the usual refractive index effects giving rise to an increase in shine on hair because the solution of the brightener in the dimethicone/cyclomethicone mixture did not possess a measurably different refractive index.

Lipstick Evaluation 0.1 g of a mixture of 0.50 g of Uvitex OB® in 49.50 g of dimethicone was added to 9.9 g of a wax based simulation of a commercial long lasting lip color formulation, Revlon Color Stay®. This preparation was repeated using the Uvitex OB® at the same levels in an alkylmethicone, which was then added at the same weight percent level to the same lipstick, as a second formulation to be evaluated. The lipstick ingredients were melted together, the fluorescent brightener added with good stirring, and the molten formulation poured into a mold to cool. The products were compared in half lip evaluations and rated by in-house panelists as being noticeably brighter in color intensity than the control side which was exactly the same formulation without the fluorescent brightener added.

All United States patents referenced herein are herewith and hereby incorporated by reference.

Having described the invention that which is claimed is:
1. A method for increasing the shine on hair comprising:
   1) formulating a cosmetic composition for application to human hair and
   2) adding thereto a fluorescent brightening agent selected from the group consisting of:
   1) 2, 2'-(2, 5-thiophene diyl)bis(5-tert-butylbenzoxazole); and
   2) 2, 2'-(1, 1-ethlene bis(3-sulfo-4, 1-phenylene)imino(6-(diethyl amino)-1, 3, 5-triazine4, 2-di-yl)imino))bis-1, 4-benzene-di-sulfonic acid, hexa-sodium salt.
2. A method according to claim 1 where said fluorescent brightening agent is added in an amount ranging from about 0.0005 to about 5.000 % by weight of the total weight of said cosmetic composition.
3. The method of claim 2 where the cosmetic composition is selected from the group consisting of hair conditioners, hair mousses, hair fixatives, hair sprays, hair gels, hair creams, and hair cuticle coats.
4. The method of claim 3 where said cosmetic composition further contains a solvent selected from the group consisting of
1-methyl-2-pyrrolidinone, 1N acetic acid
n-butanol,
alkyl methicones,
cyclohexane,
cyclomethicone,
diethylene glycol,
diethylene glycol monobutylether
dimethiconol,
dimethicone,
dipropylene glycol,
95 % ethanol,
ethoxy diglycol,
ethoxyethanol,
ethyl acetate,
n-heptane,
n-hexane,
0.1N hydrochloric acid,
iso-propanol,
methyl ethyl ketone,
phenyltrimethicone,
tetrahydronaphthalene,
triethylene glycol,
water and mixtures thereof.

5. A method for increasing the color intensity of a cosmetic composition comprising:
1) formulating a cosmetic composition for application to the human body and
2) adding thereto a fluorescent brightening agent, selected from the group consisting of:
1) 2,2'-(2,5-thiophene diyl)bis(5-tert-butylbenzoxazole); and
2) 2,2'-(1'1-ethylene bis(3-sulfo-4,1-phenylene)imino (6-(diethyl amino)-1,3,5-triazine-4,2-diyl)imino)) bis-1,4-benzene-di-sulfonic acid, hexa-sodium salt.

6. A method according to claim 5 where said fluorescent brightening agent is added in an amount ranging from about 0.0005 to about 5.000 % by weight of the total weight of said cosmetic composition.

7. The method of claim 6 where said cosmetic composition further contains a solvent selected from the group consisting of
1-methyl-2-pyrrolidinone,
1N acetic acid
n-butanol,
alkyl methicones,
cyclohexane,
cyclomethicone,
diethylene glycol,
diethylene glycol monobutylether
dimethiconol,
dimethicone,
dipropylene glycol,
95 % ethanol,
ethoxy diglycol,
ethoxyethanol,
ethyl acetate,
n-heptane,
n-hexane,
0.1N hydrochloric acid,
iso-propanol,
methyl ethyl ketone,
phenyltrimethicone,
tetrahydronaphthalene,
triethylene glycol,
water and mixtures thereof.

8. The method of claim 7 where the color cosmetic composition is selected from the group consisting of nail lacquers and lipsticks.

9. A color cosmetic composition comprising a fluorescent brightening compound selected from the group consisting of:
1) 2, 2'-(2, 5-thiophene diyl)bis(5-tert-butylbenzoxazole); and
2) 2, 2'-(1, 1-ethylene bis(3-sulfo-4, 1-phenylene)imino (6-(diethvl amino)-1, 3, 5-triazine-4, 2-di-yl)imino)) bis-1, 4-benzene-di-sulfonic acid, hexa-sodium salt and solvent.

* * * * *